US011485947B2

(12) United States Patent
Ali

(10) Patent No.: US 11,485,947 B2
(45) Date of Patent: Nov. 1, 2022

(54) HOLLOW FIBER FILTER ARRANGEMENT

(71) Applicant: Global Life Sciences Solutions USA LLC, Marlborough, MA (US)

(72) Inventor: Yasser Ali, Westborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 562 days.

(21) Appl. No.: 15/609,787

(22) Filed: May 31, 2017

(65) Prior Publication Data

US 2018/0346861 A1  Dec. 6, 2018

(51) Int. Cl.
| | | |
|---|---|---|
| *C12M 3/00* | (2006.01) | |
| *C12M 1/00* | (2006.01) | |
| *C12M 1/12* | (2006.01) | |
| *B01D 65/00* | (2006.01) | |
| *B01D 63/02* | (2006.01) | |
| *B01D 29/11* | (2006.01) | |
| *B01D 35/30* | (2006.01) | |

(52) U.S. Cl.
CPC ........... *C12M 25/02* (2013.01); *B01D 29/117* (2013.01); *B01D 35/30* (2013.01); *B01D 63/02* (2013.01); *B01D 65/00* (2013.01); *C12M 23/14* (2013.01); *C12M 23/26* (2013.01); *C12M 29/16* (2013.01); *B01D 2313/20* (2013.01); *B01D 2313/23* (2013.01); *B01D 2313/58* (2013.01)

(58) Field of Classification Search
CPC ...... B01D 63/02; B01D 65/00; B01D 29/117; B01D 35/30; B01D 2313/58; B01D 2313/23; B01D 2313/20; C12M 23/14; C12M 29/16; C12M 25/02; C12M 23/26
See application file for complete search history.

(56) References Cited

U.S. PATENT DOCUMENTS

| | | | |
|---|---|---|---|
| 2012/0238011 A1* | 9/2012 | Tuohey et al. | ........ C12M 23/26 435/297.1 |
| 2013/0059371 A1* | 3/2013 | Shevitz | .................. C12M 29/16 435/297.4 |
| 2016/0194589 A1* | 7/2016 | Liderfelt et al. | ....... C12M 23/14 435/289.1 |

\* cited by examiner

*Primary Examiner* — Nathan A Bowers
(74) *Attorney, Agent, or Firm* — Eversheds Sutherland (US) LLP

(57) ABSTRACT

Disclosed is a hollow fiber filter arrangement and a bioreactor system comprising such a hollow fiber filter arrangement. The hollow fiber filter arrangement comprising: an inlet for receiving a sample to be filtered in the hollow fiber filter arrangement; an outlet for delivering of the filtered sample out from the hollow fiber filter arrangement; a bundle of elongate hollow fibers connected at a first end to the inlet and connected at an opposite second end to the outlet; and an outer housing enclosing the bundle, wherein a filtrate/waste collection space is provided between the outer housing and the at least one elongated hollow fiber, and wherein the outer housing is made from a flexible material.

20 Claims, 7 Drawing Sheets

HOLLOW FIBER FILTER ARRANGEMENT

TECHNICAL FIELD OF THE INVENTION

The present invention relates to a hollow fiber filter arrangement and to a bioreactor system, for example used in cell culture.

RELATED ART

Hollow fiber filter systems comprise conventionally a bundle of hollow fibers inside an enclosing rigid cartridge. The hollow fibers are commonly produced using artificial polymers and they are semi-permeable, i.e. allows particles to pass through their walls in dependence of the size of the particles. Hollow fiber filters can be used for liquid and gaseous filtration and are for example used for water treatment, cell culture and medicine.

In cell culturing a hollow fiber filter cartridge can for example be connected to a bioreactor for filtering out waste from the cell culture. Cells will be retained in the passages within the hollow fiber filter and be transferred back into the bioreactor as retainate having passed from one side of the fibres' passages to the other, and smaller waste particles will pass out through the hollow fibers' walls as filrate and will be transferred to a waste bag and not be returned to the bioreactor.

SUMMARY OF THE INVENTION

It is an object of embodiments of the invention to provide an improved hollow fiber filter arrangement.

It is a further object of embodiments of the invention to provide a lower cost hollow fiber filter arrangement.

It is a further object of embodiments of the invention to provide an improved bioreactor system.

The objects are addressed by a hollow fiber filter arrangement and a bioreactor system according to the independent claims.

In embodiments a flexible elongate outer housing part can be provided, which is lower in cost than a conventional rigid outer housing. Furthermore the flexible elongate outer housing part can be provided in different sizes and thereby the hollow fiber filter arrangement can in some applications be used also as a waste bag.

A bioreactor system comprising a bioreactor connected to a hollow fiber filter arrangement according to embodiments of the invention provides a cheap and flexible bioreactor system. Such a bioreactor system is suitable for use as a single use bioreactor system, i.e. a system which is manufactured with the intension that it will be used only once, then discarded.

According to one aspect of the invention a hollow fiber filter arrangement is provided comprising:
- an inlet for receiving a sample to be filtered in the hollow fiber filter arrangement;
- an outlet for delivering of the filtered sample out from the hollow fiber filter arrangement;
- at least one elongated hollow fiber connected in a first end of its elongated extension to the inlet of the hollow fiber filter arrangement and connected in an opposite second end of its elongated extension to the outlet of the hollow fiber filter arrangement; and
- an outer housing enclosing said at least one elongated hollow fiber, wherein a waste collection space is provided between the outer housing and the at least one elongated hollow fiber, wherein the outer housing comprises an elongate outer housing part which surrounds substantially the whole length of the at least one elongated hollow fiber, wherein said elongate outer housing part is made from a flexible material.

According to another aspect of the invention a bioreactor system is provided comprising a bioreactor bag comprising a cell culture, wherein said bioreactor system further comprises a hollow fiber filter arrangement as described above, wherein the inlet of the hollow fiber filter arrangement is connected to a pump unit which is configured for pumping the cell culture through the hollow fiber filter arrangement for removal of waste from the cell culture.

In one embodiment of the invention said outer housing of the hollow fiber filter arrangement further comprises a first and a second end fitment, wherein said first end fitment comprises the inlet and is connected to a first end of the elongate outer housing part and said second end fitment comprises the outlet and is connected to a second end of the elongate outer housing part such that the elongate outer housing part together with the first and second end fitments enclose the at least one elongate hollow fiber.

In one embodiment of the invention said elongate outer housing part comprises two flexible sheets which are welded to each other and to the first and second end fitments.

In one embodiment of the invention one of the flexible sheets is a wall in a flexible bioreactor bag. Hereby a bioreactor system id provided wherein the hollow fiber filter arrangement is provided within the bioreactor bag and the inlet of the hollow fiber filter arrangement is connected to an outlet from the bioreactor bag via the pump and the outlet of the hollow fiber filter arrangement is left unconnected within the bioreactor bag for delivering filtered cells into the bioreactor bag. Furthermore, in this embodiment of the invention the elongate outer housing part of the hollow fiber filter arrangement comprises a waste outlet connected through a wall of the bioreactor bag to an external waste bag and the elongate outer housing part comprises two flexible sheets welded to each other to enclose the at least one elongate hollow fiber wherein one of the flexible sheets is a wall in the bioreactor bag.

By using one of the bioreactor flexible walls as a part of the elongate outer housing part the hollow fiber filter arrangement according to the invention can easily be incorporated inside a bioreactor. Such a bioreactor system would reduce the risk of cell-loss during a cell cultivation process. Furthermore cell viability would be improved compared to conventional bioreactor systems comprising integrated tangential flow perfusion filters. There will also be less problem related to filter-clogging and fouling in a bioreactor system comprising an integrated flexible hollow fiber according to the invention.

In one embodiment of the invention said first and second end fitments are boat shaped and made from a more stable material than the elongate outer housing part. Said first end fitment can comprise a first hollow fiber receiving part configured for holding the first end of the at least one elongated hollow fiber and said second end fitment can comprises a second hollow fiber receiving part configured for holding the second end of the at least one elongated hollow fiber.

In one embodiment of the invention said at least one elongated hollow fiber is a bundle of elongated hollow fibers provided within a protecting sleeve.

In one embodiment of the invention said elongate outer housing part comprises a waste outlet.

In one embodiment of the invention the dimensions of the outer housing is chosen such that the hollow fiber filter arrangement can be used as waste bag as well as filter.

In one embodiment of the invention the flexible material of the elongate outer housing part is a composite film designated to provide strength, flexibility, gas barrier and inert fluid contact e.g. ethylene vinyl acetate (EVA), polyethylene vinyl alcohol (PVA) or ultra-low-density polyethylene (LDPE).

BRIEF DESCRIPTION OF THE DRAWINGS

FIG. 1b is a perspective view of the same hollow fiber filter arrangement as shown in FIG 1a.

DETAILED DESCRIPTION OF THE EMBODIMENTS

Figure 1A:
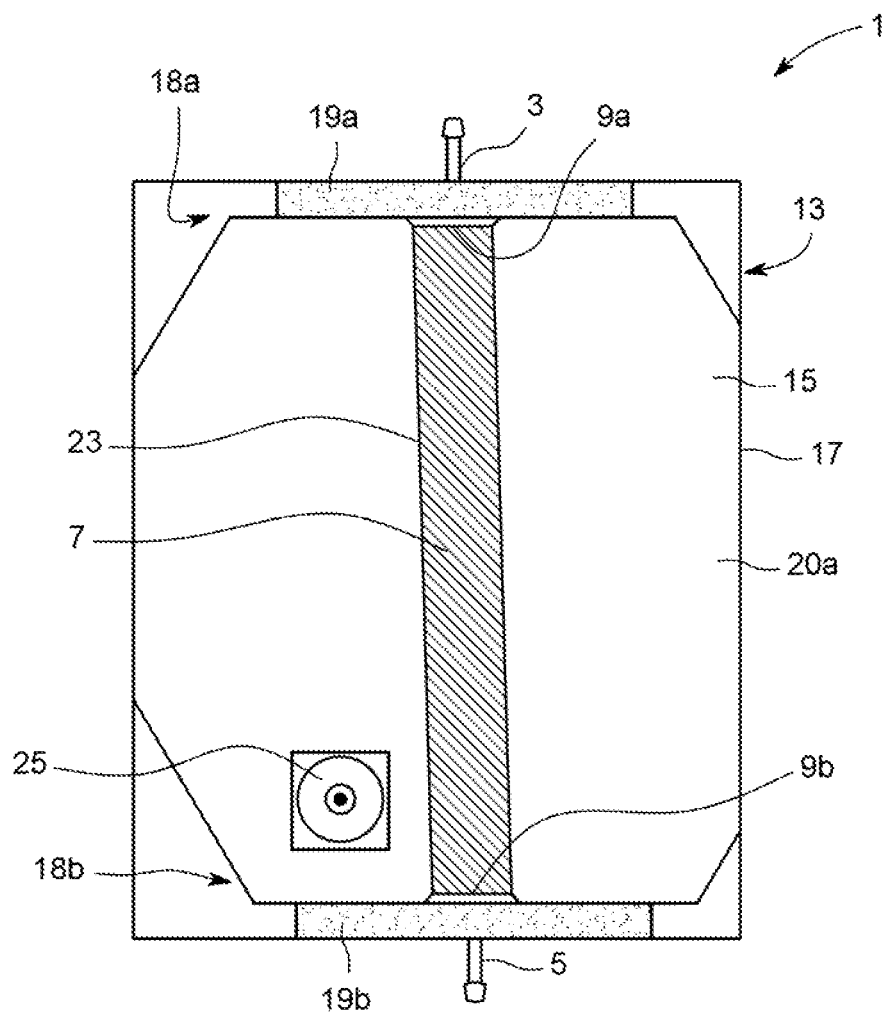
FIG. 1a is a schematic side view of a hollow fiber filter arrangement according to one embodiment of the invention.
Figure 1B:
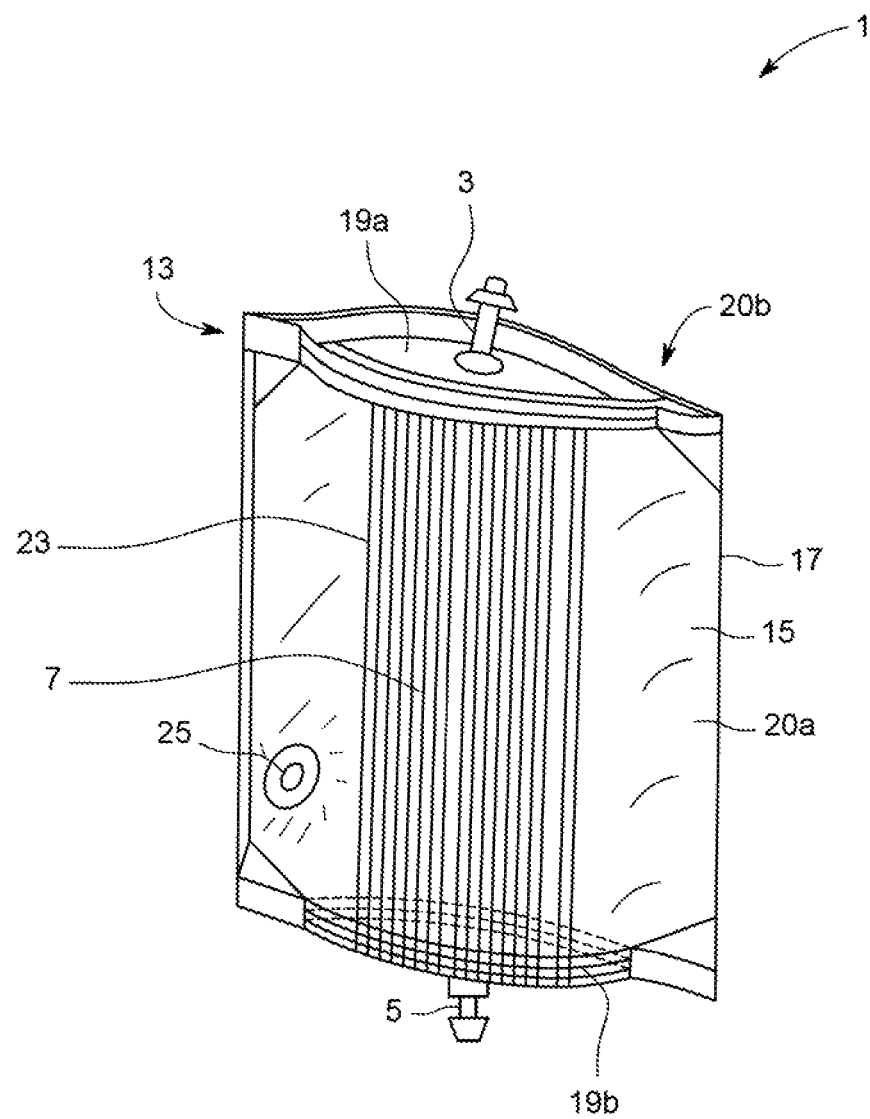

FIG. 1a is a schematic side view of a hollow fiber filter arrangement 1 according to one embodiment of the invention. FIG. 1b is a perspective view of the same hollow fiber filter arrangement 1 as shown in FIG. 1a. The hollow fiber filter arrangement 1 comprises an inlet 3 for receiving a sample to be filtered in the hollow fiber filter arrangement and an outlet 5 for delivering of the filtered sample out from the hollow fiber filter arrangement 1. The sample could be for example a cell culture where waste should be filtered from the cells.

The hollow fiber filter arrangement 1 comprises further at least one elongated hollow fiber 7 connected in a first end 9a of its elongated extension to the inlet 3 of the hollow fiber filter arrangement 1 and connected in an opposite second end 9b of its elongated extension to the outlet 5 of the hollow fiber filter arrangement 1. The number of hollow fibers in the fiber filter arrangement 1 can vary between one and hundreds depending on diameter of the fibers and depending on application. The hollow fibers are provided as a bundle of fibers and are connected to the same inlet 3 and outlet 5. In one embodiment, but not necessarily, the hollow fibers are provided within a protecting sleeve 23. The protecting sleeve can be made from a slightly more stable material than the hollow fibers themselves in the form of for example a cylindrical net or and other shapes to protect the fragile hollow fibers from any damage post manufacturing and during shipment and storage process.

The hollow fiber filter arrangement 1 comprises further an outer housing 13 enclosing said at least one elongated hollow fiber 7. A waste collection space 15 is hereby provided between the outer housing and the at least one elongated hollow fiber 7. In this waste collection space 15 content which has passed out through the hollow fiber filter walls will be collected. This can for example be waste separated out from a cell culture where the cells will be kept inside the hollow fibers and pass out through the outlet 5 of the hollow fiber filter arrangement 1. The outer housing 13 comprises an elongate outer housing part 17 which surrounds substantially the whole length of the at least one elongated hollow fiber 7 and according to the invention said elongate outer housing part 17 is made from a flexible material. The flexible material can for example be a composite film designated to provide strength, flexibility, gas barrier and inert fluid contact e.g. ethylene vinyl acetate (EVA), polyethylene vinyl alcohol (PVA) and ultra-low-density polyethylene (LDPE).

In one embodiment of the invention said elongate outer housing part 17 comprises a waste outlet 25. Hereby the waste can be removed from the hollow fiber filter arrangement and further transferred to for example a waste bag. However in another embodiment no filtrate outlet 25 is provided but instead the dimensions of the outer housing 13 is chosen such that the hollow fiber filter arrangement can be used as waste bag as well as filter. The dimension of the outer housing 13 can be chosen to suit each specific application. If the hollow fiber filter arrangement will be used as a single use filter in a disposable system the size of the waste collection space 15 needs to be provided such that all waste which will be removed from the system during the application period will fit into the waste collection space 15.

The outer housing 13 comprises further a first and a second end fitment 19a, 19b, wherein said first end fitment 19a comprises the inlet 3 and is connected to a first end 18a of the elongate outer housing part 17 and said second end fitment 19b comprises the outlet 5 and is connected to a second end 18b of the elongate outer housing part 17 such that the elongate outer housing part 17 together with the first and second end fitments 19a, 19b enclose the at least one elongate hollow fiber 7.

In the embodiment shown in FIGS. 1a and 1b said elongate outer housing part 17 comprises two flexible sheets 20a, 20b which are welded to each other and to the first and second end fitments 19a, 19b. I.e. outer long sides of the flexible sheets 20a, 20b are welded to each other and upper and lower (referring to directions in the drawing) short ends are welded to the first and second end fitments 19a, 19b respectively. Hereby the two flexible sheets 20a, 20b will enclose the at least one elongated hollow fiber 7 along substantially the whole length of the at least one (or bundle of) elongated hollow fiber(s) and a waste collection space 15 is provided there between as described above. Herein the term flexible is intended to encompass material which flexes without undue force, e.g. flexible by fluidic forces encountered when fluids fill the housing and move around, causing the housing to flex under the influence only of the fluidic forces. Such flexing is advantageous in cell culture, because there is then reduced stress exerted on cells which contact the flexible housing.

Figure 2A:
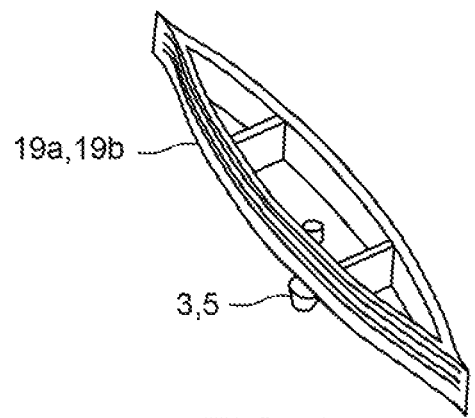
FIGS. 2a-2c shows one embodiment of a first and second end fitment according to the invention.
Figure 2B:
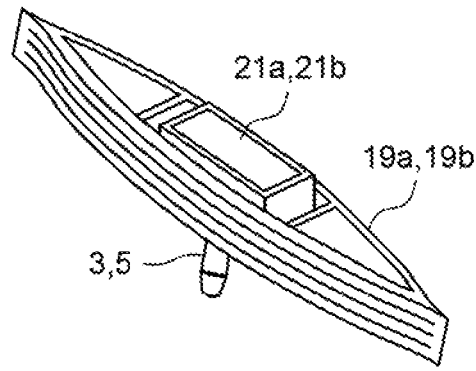
Figure 2C:
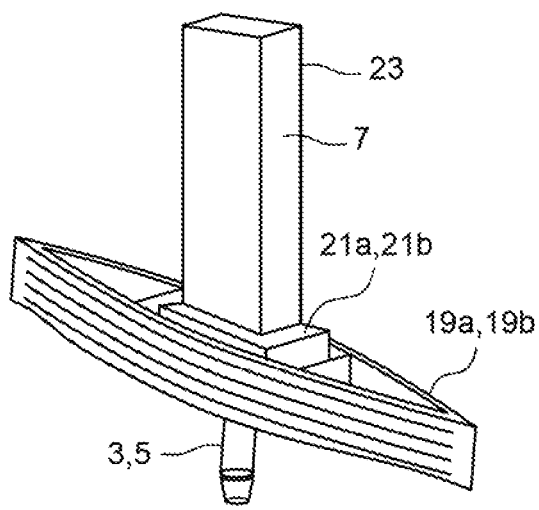

FIGS. 2a-2c show one embodiment of a first and second end fitment 19a, 19b according to the invention which for example can be used in the hollow fiber filter arrangement 1 according to the embodiment as shown in FIGS. 1a and 1b. In this embodiment the first and second end fitments 19a, 19b are boat shaped and made from a more stable material than the elongate outer housing part 17. The material can be for example polyethylene. Said first end fitment 19a can comprise a first hollow fiber receiving part 21a configured for holding the first end 9a of the at least one elongated hollow fiber 7 and said second end fitment 19b can comprise a second hollow fiber receiving part 21b configured for holding the second end 9b of the at least one elongated hollow fiber 7. In this embodiment of the invention the first and second hollow fiber receiving parts 21a, 21b are provided inside the boat shaped first and second end fitments 19a, 19b respectively and are connected to the inlet 3 and the outlet 5 respectively. If a protecting sleeve 23 is provided around the at least one elongate hollow fiber this protecting sleeve 23 can also be provided into the first and second hollow fiber receiving parts 21a, 21b respectively.

Figure 3:
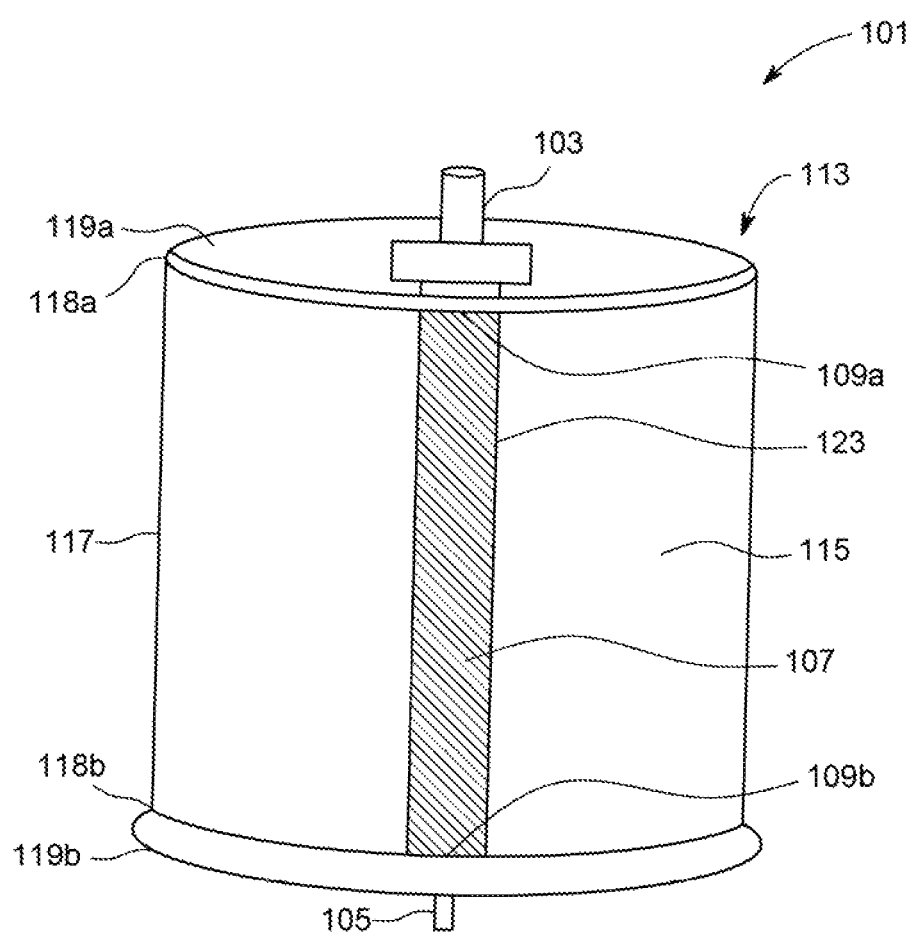
FIG. 3 shows schematically a hollow fiber filter arrangement according to another embodiment of the invention.

FIG. 3 shows schematically a hollow fiber filter arrangement 101 according to another embodiment of the invention. Many of the parts are the same or similar to the embodiment as described in relation to FIGS. 1a and 1b and are given corresponding reference numbers. Hereby the inlet 103, the outlet 105, the at least one elongate hollow fiber 107 and its extension between the inlet 103 and the outlet 105 and a possible protection sleeve 123 will not be described in detail again. A difference in this embodiment is that the elongate outer housing part 117 of the outer housing 113 is not comprised of two flexible sheets as in the previous embodiment but comprises instead a cylindrical, flexible wall 117. A first end 118a of the elongate outer housing part 117 is as in the previously described embodiment connected to a first end fitment 119a and a second end 118b of the elongate outer housing part 117 is connected to a second end fitment 119b. The outer housing 113 comprises the elongate outer housing part 117 and the first and second end fitments 119a, 119b and together they enclose the at least one elongate hollow fiber 107. The first and second end fitments 119a, 119b are in this embodiment circular for fitting to the cylindrical form of the elongate outer housing part 117. Hereby the first and second ends 118a, 118b of the elongate outer housing part 117 will be connected to an outer circumference of the first and second end fitments 119a, 119b respectively. The first and second end fitments 119a, 119b can each comprise a hollow fiber receiving part for holding the at least one elongate hollow fiber and connect them to the inlet 103 and the outlet 105 respectively in the same or a similar way as described above for the embodiment described in relation to FIGS. 2a-2c.

Other geometries of the hollow fiber filter arrangement than the two described above in relation to FIGS. 1 and 3 are also possible. For example the hollow fiber filter arrangement can instead have a square, rectangle or hexagonal cross section.

Figure 4:
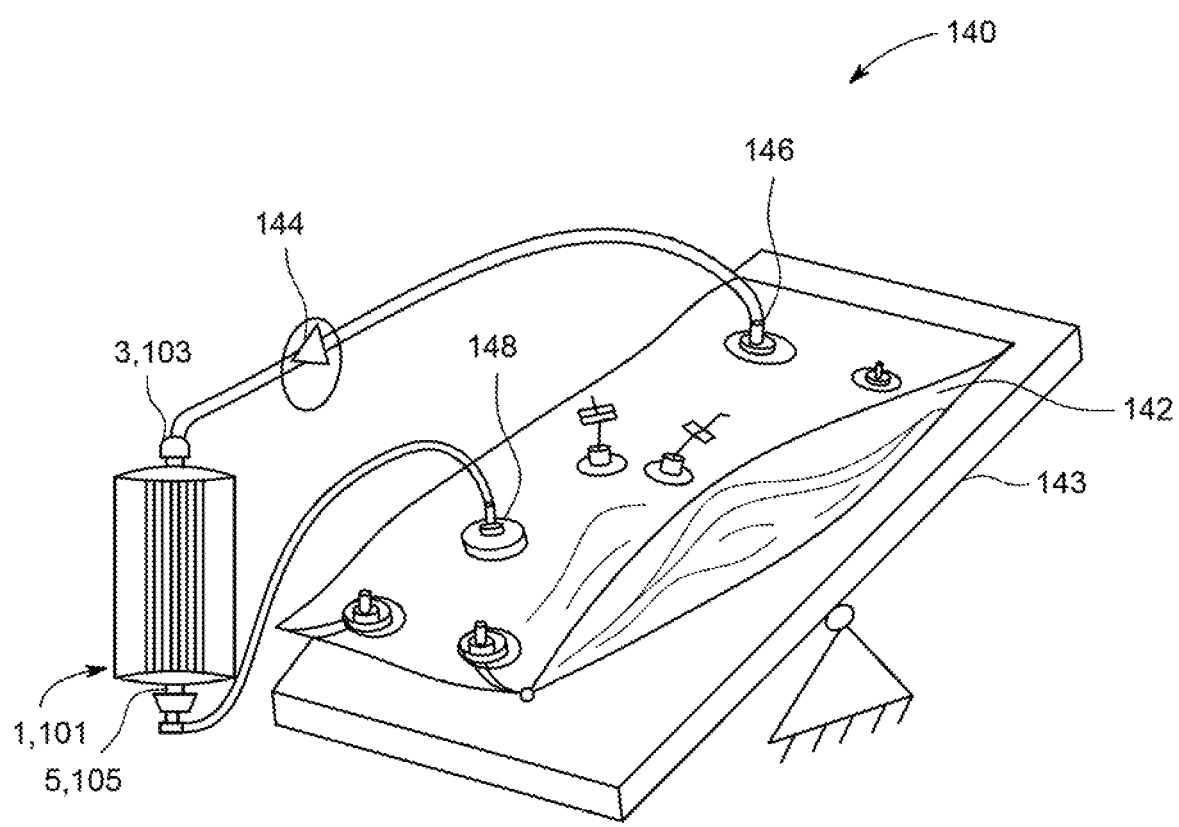
FIG. 4 shows schematically a bioreactor system comprising a hollow fiber filter arrangement according to one embodiment of the invention.

FIG. 4 shows schematically a bioreactor system 140 comprising a hollow fiber filter arrangement 1; 101 according to one embodiment of the invention. The hollow fiber filter arrangement 1; 101 can be any of the embodiments described above. The bioreactor system 140 comprises a bioreactor bag 142 comprising a cell culture. In this embodiment the bioreactor bag 142 is a flexible bag provided onto a rocking station 143. However other bioreactor bags can also be used in this invention, such as bioreactor bags provided with a stirring mechanism inside the bioreactor instead of the rocking station. The inlet 3; 103 of the hollow fiber filter arrangement 1; 101 is connected to an outlet 146 from the bioreactor bag 142 via a pump 144 and the outlet 5; 105 of the hollow fiber filter arrangement 1; 101 is connected to an inlet 148 to the bioreactor bag 142. The pump unit 144 is configured for pumping the cell culture through the hollow fiber filter arrangement 1; 101 for removal of waste from the cell culture.

In this embodiment no waste outlet 25 is shown on the hollow fiber filter arrangement 1; 101. However such a waste outlet 25 could be provided also in this embodiment. If no waste outlet is provided the dimensions and geometry of the outer housing 13; 213 of the hollow fiber filter arrangement 1; 101 should be chosen to suit the specific application performed in the bioreactor system 140. If for example cells should be cultured to a certain extent and then delivered for further use the outer housing 13; 113 of the hollow fiber filter arrangement 1; 101 can be dimensioned to be able to keep all the waste that will be removed from the system during this application time. Hereby no extra waste bag is needed. Afterwards, after harvesting of the viable cells at the end of the cultivation process, both the bioreactor bag 142 and the hollow fiber filter arrangement 1; 101 can possibly be disposed of.

Figure 5A:
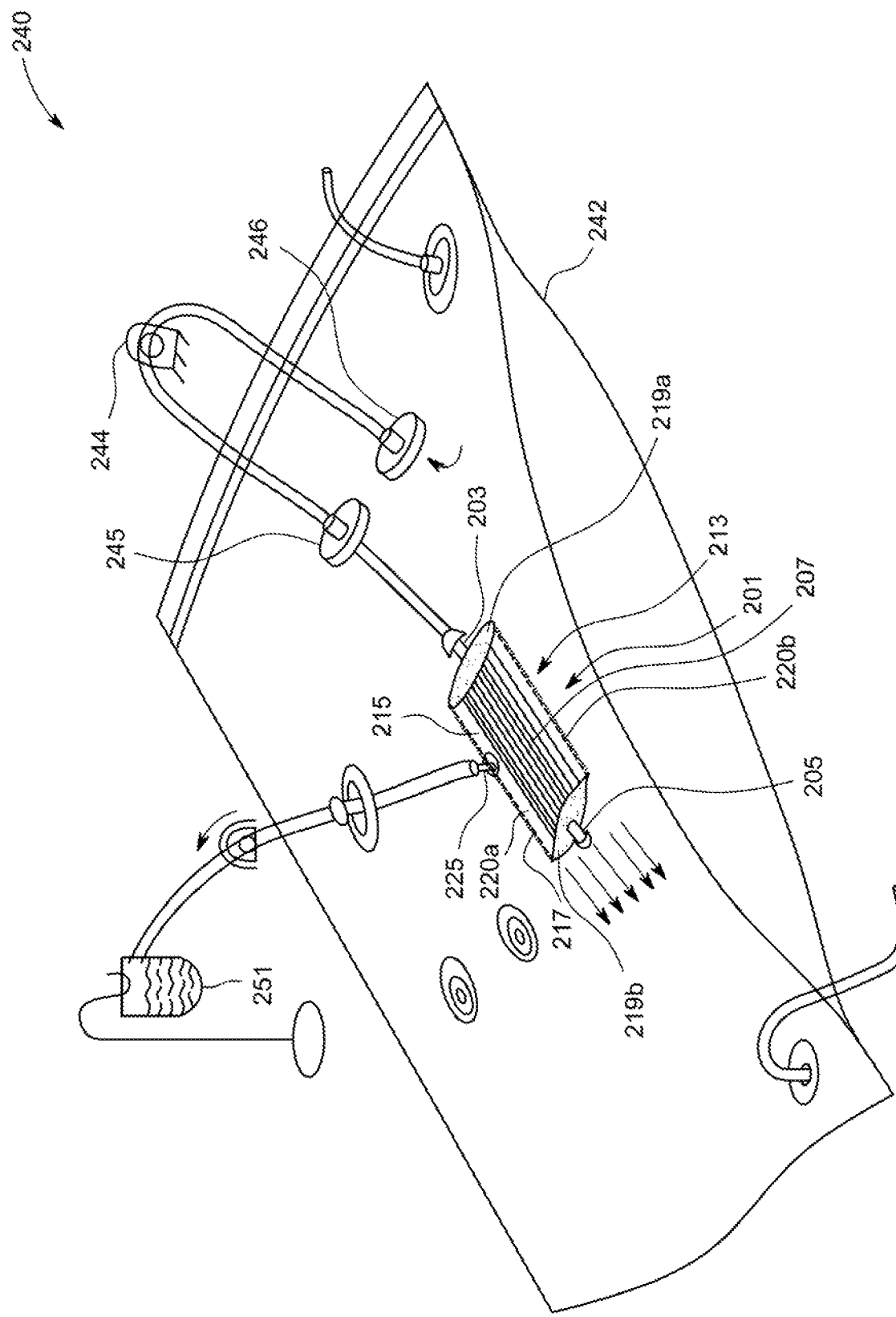
FIGS. 5a and 5b show schematically two different views of a bioreactor system comprising a hollow fiber filter arrangement according to another embodiment of the invention.
Figure 5B:
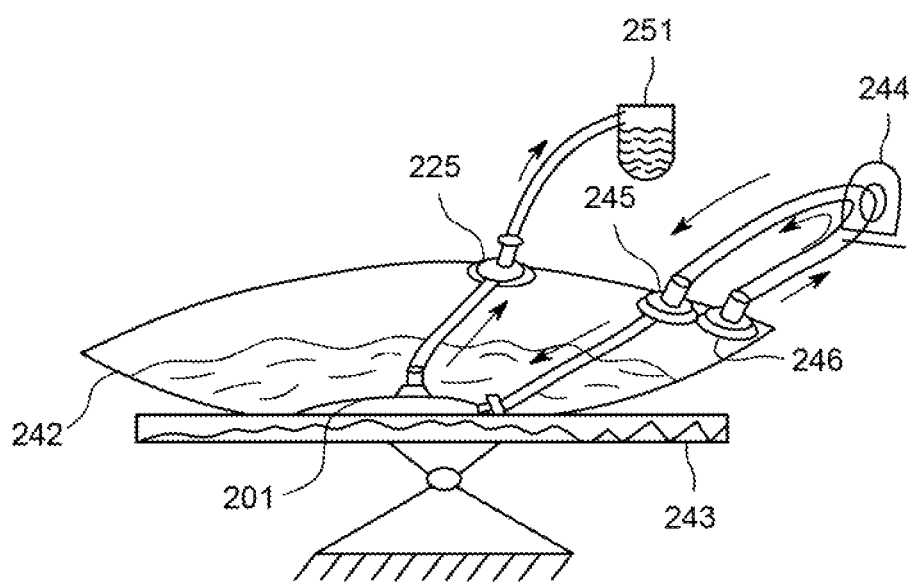

FIGS. 5a and 5b show schematically two different views of a bioreactor system 240 comprising a hollow fiber filter arrangement 201 according to another embodiment of the invention. The bioreactor system 240 comprises a bioreactor bag 242 comprising a cell culture. Also in this embodiment the bioreactor bag 242 is a flexible bag provided onto a rocking station 243. In this embodiment the hollow fiber filter arrangement 201 is provided inside the bioreactor bag 242. The hollow fiber filter arrangement 201 is similar to the hollow fiber filter arrangement 1 described in relation to FIGS. 1a and 1b and similar parts are given similar numbers and will not be described in detail. An elongate outer housing part 217 of the outer housing 213 comprises in this embodiment two flexible sheets 220a, 220b which are welded to each other and to a first and a second end fitment 219a, 219b in order to enclose the at least one elongate hollow fiber 207 of the hollow fiber filter arrangement 201 in a similar way as described above in relation to FIGS. 1a and 1b. However in this embodiment one of the flexible sheets 220b is a wall in the bioreactor bag 242.

An inlet 203 of the hollow fiber filter arrangement 201 is connected to a port 245 in a wall of the bioreactor bag 242. Said port 245 is further connected to an outlet port 246 from the bioreactor bag 242 via a pump 244. The pump 244 is provided outside the bioreactor bag 242. Hereby the content of the bioreactor bag 242 can be pumped through the hollow fiber filter arrangement 201. An outlet 205 of the hollow fiber filter arrangement 201 is left unconnected within the bioreactor bag 242 for delivering filtered cells into the bioreactor bag.

The elongate outer housing part 217 of the hollow fiber filter arrangement 201 comprises further in this embodiment a waste outlet 225 connected through a wall of the bioreactor bag 242 to an external waste bag 251. Hereby waste collected in a waste collection space 215 of the hollow fiber filter arrangement 201 can be transferred to an external waste bag 251.

A bioreactor system 240 according to this embodiment where a hollow fiber filter arrangement 201 having a flexible outer housing is provided inside the bioreactor bag 242 provides for a convenient and cheap bioreactor system where continuous waste removal is achieved.

While viable cells will be retained in the bioreactor system 240, toxic metabolic by-products and cell debris are continuously removed. Feed, containing nutrients is continually added to the bioreactor system 240 to achieve high cell densities with high viability for long time without transferring the cells outside of the bioreactor. This technique is very useful for cultivating slow-growing cells.

The invention claimed is:

1. A hollow fiber filter arrangement comprising:
    an inlet for receiving a sample to be filtered in the hollow fiber filter arrangement;
    an outlet for delivering the filtered sample out from the hollow fiber filter arrangement;
    at least one elongated hollow fiber connected at a first end to the inlet and connected at an opposite second end to the outlet; and an outer housing enclosing the at least one elongated hollow fiber such that a filtrate collection space substantially surrounds the at least one elongated hollow fiber, wherein the outer housing comprises:
an elongate outer housing part made from a flexible material;
a first end fitment connected to a first end of the elongate outer housing part; and
a second end fitment connected to a second end of the elongate outer housing part;
wherein the first end fitment and the second end fitment each have an elongated boat shape defined by a first curved sidewall and a second curved sidewall connected to one another at opposite ends of the boat shape.

2. The hollow fiber filter arrangement according to claim 1, wherein the first end fitment comprises the inlet, and wherein the second end fitment comprises the outlet.

3. The hollow fiber filter arrangement according to claim 1, wherein the elongate outer housing part comprises two flexible sheets which are welded to one another and to each of the first end fitment and the second end fitment.

4. The hollow fiber filter arrangement according to claim 3, wherein one of the flexible sheets is a wall in a flexible bioreactor bag.

5. The hollow fiber filter arrangement according to claim 1, wherein the first end fitment and the second end fitment are made from a more rigid material than the elongate outer housing part.

6. The hollow fiber filter arrangement according to claim 1, wherein the first end fitment comprises a first hollow fiber receiving part configured for holding the first end of the at least one elongated hollow fiber, and wherein the second end fitment comprises a second hollow fiber receiving part configured for holding the second end of the at least one elongated hollow fiber.

7. The hollow fiber filter arrangement according to claim 1, wherein the at least one elongated hollow fiber is a bundle of elongated hollow fibers provided within a protecting sleeve.

8. The hollow fiber filter arrangement according to claim 1, wherein the elongate outer housing part comprises a filtrate or waste outlet.

9. The hollow fiber filter arrangement according to claim 1, wherein the outer housing is sized such that the hollow fiber filter arrangement can be used as a waste bag as well as a filter.

10. The hollow fiber filter arrangement according to claim 1, wherein the flexible material of the elongate outer housing part is a composite film.

11. The hollow fiber filter arrangement according to claim 1, wherein the flexible material of the elongate outer housing part comprises ethylene vinyl acetate (EVA), polyethylene vinyl alcohol (PVA), or ultra-low-density polyethylene (LDPE).

12. The hollow fiber filter arrangement according to claim 11, wherein the first end fitment and the second end fitment are made from polyethylene (PE).

13. The hollow fiber filter arrangement according to claim 1, further comprising a sleeve surrounding the at least one elongated hollow fiber, wherein the sleeve is made from a more rigid material than the at least one elongated hollow fiber.

14. The hollow fiber filter arrangement according to claim 13, wherein the first end fitment comprises a first hollow fiber receiving part configured for holding the first end of the at least one elongated hollow fiber and a first end of the sleeve, and wherein the second end fitment comprises a second hollow fiber receiving part configured for holding the second end of the at least one elongated hollow fiber and a second end of the sleeve.

15. A bioreactor system comprising a bioreactor bag suitable for cell culture and the hollow fiber filter arrangement according to claim 1, wherein the inlet of the hollow fiber filter arrangement is connected to a pump unit which is configured for pumping the cell culture through the hollow fiber filter arrangement for removal of waste from the cell culture.

16. The bioreactor system according to claim 15, wherein the inlet of the hollow fiber filter arrangement is connected to an outlet of the bioreactor bag via the pump, and wherein the outlet of the hollow fiber filter arrangement is connected to an inlet of the bioreactor bag.

17. The bioreactor system according to claim 15, wherein the hollow fiber filter arrangement is provided within the bioreactor bag, wherein the inlet of the hollow fiber filter arrangement is connected to an outlet of the bioreactor bag via the pump, and wherein the outlet of the hollow fiber filter arrangement discharges into the bioreactor bag for delivering retained cells into the bioreactor bag.

18. The bioreactor system according to claim 17, wherein the elongate outer housing part of the hollow fiber filter arrangement comprises a waste outlet connected through a wall of the bioreactor bag to an external waste bag, wherein the elongate outer housing part comprises two flexible sheets welded to each other to enclose the at least one elongated hollow fiber, and wherein one of the flexible sheets is a wall in the bioreactor bag.

19. A cell culture method comprising:
providing a flexible cell culture bioreactor bag;
providing the hollow fiber filter arrangement according to claim 1 within the bioreactor bag; and
culturing cells in the bioreactor bag suspended in a liquid culture medium while rocking the bioreactor bag.

20. The cell culture method according to claim 19, further comprising repeatedly or continuously passing the suspension through the hollow fiber filter arrangement.

* * * * *